United States Patent [19]

Sharma

[11] Patent Number: 5,225,182

[45] Date of Patent: Jul. 6, 1993

[54] VECTORED DRUG DELIVERY SYSTEM USING A CEPHALOPLASTIN LINKING AGENT AND A METHED OF USING THE SYSTEM

[76] Inventor: Yash P. Sharma, 8210 Labbe La., Vienna, Va. 22180

[21] Appl. No.: 786,044

[22] Filed: Oct. 31, 1991

[51] Int. Cl.$^5$ .............. A61K 37/00; A61K 49/00; C07K 3/08; C07K 17/00
[52] U.S. Cl. ................... 424/9; 424/85.91; 514/12; 530/362; 530/363
[58] Field of Search ............ 424/85.91, 9; 514/12; 530/362, 363, 387

[56] References Cited

U.S. PATENT DOCUMENTS 4,360,358  11/1982  Sharma ........................ 23/230
4,867,973  9/1989  Geors et al. ................. 424/85.91

FOREIGN PATENT DOCUMENTS 2013523  8/1979  United Kingdom .

OTHER PUBLICATIONS

Martodam, et al. PNAS 76(5) 2128-2132 1979.

*Primary Examiner*—David L. Lacey
*Assistant Examiner*—Donald E. Adams
*Attorney, Agent, or Firm*—Cushman, Darby & Cushman

[57] ABSTRACT

The subject invention relates to a novel method for vectored delivery of physiologically-active chemical agents to a target organ, tissue or cell of interest and uses thereof. In particular, medical vectoring reagents which localize in a specific target organ, tissue or cell are conjugated with a drug or therapeutic agent using a linking agent, and the resulting conjugate is then introduced into the body. The chemical agent is thereby localized in the target organ, tissue or cell for effecting a therapeutic or physiological benefit or change therein.

12 Claims, No Drawings

VECTORED DRUG DELIVERY SYSTEM USING A CEPHALOPLASTIN LINKING AGENT AND A METHED OF USING THE SYSTEM

BACKGROUND OF THE INVENTION

1. Technical Field

The subject invention relates to a novel composition and method for the vectered delivery of physiologically-active chemical agents to a mammalian target organ or tissue site of interest and to uses thereof. In particular, a combination conjugate composition is provided having the capability of localizing delivery of its therapeutic component to a specific desired target organ or tissue site and thereafter enabling such therapeutic component to exhibit and effect its medical activity at such organ or site for achievement of a therapeutic or physiological benefit.

2. Background Information

Medical science has long recognized the need to control, regulate and target the release of drugs in the body. The goals have been to provide: 1) less frequent drug administration, 2) constant and continuous therapeutic levels of a drug in the systemic circulation or at a specific target organ site, 3) a reduction in undesirable drug side effects, and 4) a reduction in the amount and dose concentration required to realize the desired therapeutic benefit.

During the past decade, a wide variety of drug delivery systems have been designed and evaluated which include, for example, 1) drug carriers based on proteins, polysaccharides, synthetic polymers, erythrocytes, DNA and liposomes, 2) microspheres containing an entrapped drug. In particular, serum albumin microspheres can be sustained and controlled by various stabilization procedures generally involving heat or chemical-crosslinking of the carrier matrix.

Of course, therapeutic agents can be administered by a multitude of routes, methods, formulations and techniques which can include the use of intrusive devices and surgical procedures. Irrespective of the method of administration, the object is to maximize the therapeutic effect of the drug while simultaneously minimizing its toxic and side effects. Potential toxic effects of the therapeutic agent and biorouting material, either in combination or separately, must also be minimized. In mammals, the therapeutic agent usually has to pass from the site of administration into the blood stream and be distributed throughout the body in order to reach its target. Unfortunately, a large dilution occurs when a drug enters the blood stream so that often the eventual concentration of the drug at the desired target location is very low.

For example, suppose that a 70 kg human has a 1 gm tumor somewhere in the body. If the blood flow per gram to that tumor was approximately equal to the average blood flow to other parts of the body, then a given antibody or drug molecule would pass through the capillaries of the tumor only once in every 70,000 circulation cycle. For a circulation cycle of 1 minute, this might be only once every 49 days. Even then, the antibody or drug molecule would be statistically unlikely to leave the bloodstream during a single capillary passage. Since other mechanisms tend to clear exogenous antibody or drug components from the body systems, it is not surprising therefore that the medicinal drug delivery achieved may be on the order of thousandths or hundredths of a percent of dose per gram of tumor. Thus, the drug or antibody becomes diluted in the body and only a small percentage of the agent reaches the tumor or tissue to which it binds thereby causing a therapeutic effect (*Cancer Metastasis: Experimental or Clinical Strategies* (Alan R. Liss, Inc.), pp.69–180 (1986)).

In addition, many drugs are subject to continuous alteration, inactivation and excretion by normal biochemical and metabolic processes. These limitations are often overcome by administering higher and/or prolonged doses of the drug; however, this technique inevitably increases the risk of side effects as uncontrolled and irregular therapeutic levels of the drug often result in the circulation.

In particular, the anticancer drugs developed in the last twenty years are quite dangerous. It is known that they do not work well in the long run and have unpleasant, untoward, and sometimes disastrous, side effects. For instance, it is presently unavoidable that patients receiving certain anti-Lymphoma drugs should also lose their hair. Targeted drugs like beta blockers, used in the treatment of angina and hypertension, are designed to interfere with beta 2 receptors in the heart tissue and avoid the beta receptors in lung and gastrointestinal tissue where they could cause serious damage. But when compared to the sophisticated targeting systems for delivery of deadly and highly toxic drugs for treatment of cancers and AIDS, the beta blockers function by a relatively simplistic mechanism.

When considering the design of an efficient drug delivery system, the manipulation of large, complex structures through the anatomical and physiological barriers of the human body, programming the drug to affix to a diseased area, for example, a tumor, while avoiding adsorption in healthy organs and tissue, penetrating the diseased cells so that the therapeutic agent can enter and kill them, and saving the drug from being consumed by components of the body's own immune system before it reaches its target are only some of the problems that are encountered.

Monoclonal antibodies have also been used as a possible means of detecting and treating tumors (Weinstein et al., *Cancer Metastasis: Experimental and Clinical Strategies* (Alan R. Liss, Inc.), pp. 169–80 (1986)). The central advantage for monoclonal antibodies over classical diagnostic agents and treatments is their possible specificity for tumor cells. Yet, clinical studies with monoclonal antibodies to date have frequently been unsatisfactory. The lack of pharmacological analysis for these agents is a major drawback. Also, the antibodies are diluted in the body subsequent to administration such that only a small percentage of those administered reach the tumor or tissue to which they are to bind and ultimately cause a therapeutic effect. Furthermore, monoclonal antibodies, like all other drugs and therapeutic agents, have only a very limited efficacy and therapeutic value unless they can be targeted to a specific target or tissue. Thus, a delivery system such as that provided by the present invention is crucial if the antibodies are to be efficacious.

Several radionucleides, radio pharmaceuticals, and other agents have been used for many years in X-ray and nuclear medicine departments. Such reagents are used to enhance the image organs or body systems such as liver, bone, kidney, brain, lungs and spleen. These imaging reagents are usually made from an target-specific transfer reagent by tagging (or labeling) it with radioactive material. For example, radioactive technicium-99 m can be linked either to macroaggregated albumin particles for imaging the lungs or to glucoheptonate for brain or kidney scans (Millon, M., "Technicium 99 m Biorouting," Nuclear Medicine Technology, 2nd ed., (Mosby Co.) pp.255–78 (1975)).

In the last few years, those in the medical imaging field have visualized and quantified biorouting materials such as glucoheptonate by gamma camera and scintigraphy. Therefore, the speed and amount of material that accumulates at any place in the body (i.e., the pharmacokinetics) are known and predictable. Within minutes of administration, such radio-imaging agents start to accumulate at their specific organ site. Depending on the target organ and the mode of uptake, many of these reagents will still be detectable for days or weeks after injection. However, such organ-specific reagents used for imaging agents do not appear to have been used or suggested for the vectored delivery of therapeutic agents.

The applicant has considered the following patents and submits that the present invention is neither disclosed nor suggested therein: U.S. Pat. No. 3,663,685, U.S. Pat. No. 3,663,687, U.S. Pat. No. 3,663,686, U.S. Pat. No. 3,707,353, U.S. Pat. No. 4,147,767, U.S Pat. No. 3,937,668, U.S Pat. No. 4,101,380, U.S. Pat. No. 4,349,530, U.S. Pat. No. 4,169,804, U.S. Pat. No. 4,115,534, U.S. Pat. No. 4,230,685, U.S. Pat. No. 4,357,259, U.S. Pat. No. 4,247,406, West German patent 1,916,704, West German patent 2,115,066, U.S. Pat. No. 4,267,234, U.S. Pat. No. 4,917,892, U.S. Pat. No. 4,016,100, U.S. Pat. No. 4,145,408, U.S. Pat. No. 4,485,054, U.S. Pat. No. 4,749,572, U.S. Pat. No. 4,772,473, U.S. Pat. No. 4,835,258, U.S. Pat. No. 3,492,212, U.S. Pat. No. 3,867,269, U.S. Pat. No. 4,275,000, U.S. Pat. No. 4,625,014, British patent 2,013,523, French patent 1,604,123 and U.S. Pat. No. 4,183,918.

All U.S. patents and publications referred to herein are hereby incorporated by reference.

SUMMARY OF THE INVENTION

The present invention now provides a novel, unobvious and unique composition and method for a vectored delivery of pharmaceuticals or chemical agents to a mammalian system, organ, tissue or cell of choice as a solution to the aforesaid problems.

This invention is based in part on the discovery that known organ or tissue specific reagents, used traditionally with imaging agents, and which specifically target and localize in a given, desired mammalian organ or tissue structure, will retain that functional capability even if linked with an entirely different chemotherapeutic agent to provide a vectored delivery of the latter to said organ or tissue. At the same time, it has been surprisingly discovered that such a combination may be made with appropriate use of a linking agent which will permit release of, or at least exhibit, little if any inhibiting effect upon the physiological or therapeutic activity of the drug component of the combination. By combining an organ specific reagent with a chemotherapeutic agent with these components having, respectively, an affinity for and an effect upon a specific organ or tissue site, advantageous specific therapeutic effects can now be realized with minimized side effects, with concentration of the delivered agent at the desired organ or tissue site, thereby permitting enhanced desired therapeutic activity and the use of decreased dosage amounts.

The present invention thus comprises, in one aspect, linking a pharmaceutically acceptable organ-specific vectoring reagent, which has the capability for localizing in a desired organ or tissue site target, to a therapeutic or chemical agent. The resulting conjugate is then administered to a patient. As used herein, the term organ-specific is to be understood as signifying specificity to either a mammalian organ or tissue-site.

Furthermore, the composition containing the organ-specific vectoring reagent, the linking agent and the drug may also be conjugated to a white blood cell or monoclonal antibody in vitro obtained from a patient and then reintroduced into that patient.

In particular, the present invention encompasses a composition for the vectored selective delivery of a therapeutically-active agent to a desired mammalian target system, organ, tissue or cell comprising a conjugate composed of a pharmaceutically-acceptable non-toxic organ-specific vectoring reagent selective for said organ tissue or cell, a linking agent entity coupled thereto and a therapeutically active-agent coupled to said linking agent. The conjugate is capable of releasing the therapeutically-agent with retention of its therapeutic activity to the organ, tissue or cell. The composition may be administered orally or intravenously.

The vectoring agent is selected from the group consisting of, for example, aggregated albumin, albumin colloid, disofenin, etidronate, phosphate, sulfur colloid, succimer, glucoheptonate, pentetate, gallium citrate, rose bengal, white blood cells, orthoiodohippurate, selenomethionine and thallous chloride.

The linking agent utilized may be, for example, cephaloplastin. The linking agent may be dissolved or brought to the proper concentration by being mixed with a suitable buffer.

The therapeutically active-agent may be selected from the group consisting of, for example, antibiotics, anti-cancer drugs, cardiac drugs, analgesics, anti-epileptic drugs, vitamins, and hormones. As noted above, the composition may also include white blood cells or monoclonal antibodies.

The present invention also includes a method of delivering a therapeutically active-agent to a target organ, tissue or cell of a patient for therapeutic activity in the organ, tissue or cell comprising administering, to the patient, a composition comprising a conjugate composed of a pharmaceutically-acceptable non-toxic organ-specific vectoring reagent selective for the organ, tissue or cell, a linking agent entity coupled thereto and an therapeutically-active agent coupled to the linking agent. The conjugate, as noted above, is capable of releasing the therapeutically active-agent with retention of its therapeutic activity to the organ, tissue or cell. The composition is administered in an amount sufficient to effect delivery thereof and to, of course, have a therapeutic effect.

The present invention also includes a method of treating cancer in a patient comprising administering to the patient an amount of a composition for the vectored selective delivery of a chemotherapeutically-active agent to a mammalian target system, organ, tissue or cell. The composition comprises a conjugate composed of a pharmaceutically-acceptable non-toxic organ-specific vectoring reagent selective for the organ, tissue or cell a linking agent entity coupled thereto and a chemotherapeutically-active agent coupled to the linking agent. The conjugate is capable of releasing the chemotherapeutically-active agent with retention of its therapeutic activity to the organ, tissue or cell. The composition is administered in an amount sufficient to effect treatment.

DETAILED DESCRIPTION OF THE INVENTION

In the novel method of the present invention, an organ-specific vectoring transport reagent is linked initially to a chemical or therapeutic agent through a conjugating or linking agent. The resulting conjugate is then introduced into a patient. The conjugate will then be transported within the body to the specific desired target organ or tissue site of interest, and the therapeutic agent will then be released from the organ-specific vectoring transfer reagent, or will at least be free to exhibit its activity and subsequently carry out its function. All of the other components of the conjugate are eventually metabolized in the body or broken down into smaller elements for excretion.

The organ-specific vectoring reagent component of the present invention should be chosen based upon the system, organ, tissue or cell which is to be affected by the therapeutic agent. For example, aggregated albumin localizes in the lung by capillary blockage since its particle size is between 15-30 microns. (Particles smaller than 15 microns pass through or diffuse out of the lung capillaries.) Thus, treatment of a patient with lung cancer, using the method of the present invention, would involve linking the aggregated albumin to an anti-cancer chemotherapeutic agent and then introducing the conjugate into the patient (see, e.g., Example XVII). The conjugate will then be vectored to and localized in the lung with subsequent release of the chemotherapeutic agent, now located at the desired tissue site, and will destroy the malignant cells.

The organ-specific reagents of the present invention may be bound to the linking agent by forming covalent bonds therewith, by passive adsorption, or by a combination of the two. The bonds between the organ-specific vectoring reagents and the linking agents are broken down by an enzyme in the blood such as trypsin, lipase or amylase once the organ-specific vectoring transfer reagent/linking agent/drug conjugate combination reaches the target organ or tissue. The particular enzyme cleaving the bond is dependent upon the organ-specific vectoring reagent utilized. For example, if aggregated albumin is used, trypsin is the enzyme response for breaking the covalent bonds referred to above.

The mechanism of action of each of the organ-specific vectoring reagents is also quite important. For example, several organ-specific vectoring reagents are absorbed into the target organ of interest by either active transport, simple diffusion, exchange diffusion, phagocytosis, absorption or capillary blockage.

Table I (below) lists several known organ or tissue-specific reagents which are suitable for use as the vectoring reagent of the present invention, the tissues in which they localize, as well as their mechanism of uptake.

TABLE I

EXAMPLES OF BIOROUTING AND MECHANISM OF UPTAKE OF RADIOPHARMAECUTIALS

| Targeting or Vectoring Reagent | Radioisotope | tissue | Mechansium of Uptake/Localization |
|---|---|---|---|
| Aggregated Albumin | Technetium-99 m | Lung | Capillary blockage |
| Aggregated Albumin | Iodine-131 | Lung | Capillary blockage |
| Albumin Colloid | Technetium-99 m | Liver, Spleen, Bone Marrow | Phagocytosis |
| Disofenin (DISIDA) | Technitium-99 m | Liver, gall bladder | Active transport |
| Etidronate (EHDP) | Technitium-99 m | Bone | Absorption |
| Phosphate | Technitium-99 m | Bone | Absorption |
| Sulfur Colloid (SC) | Technitium-99 m | Liver, Spleen, Bone Marrow | Phagocytosis |
| Succimer (DMSA) | Technitium-99 m | Kidney | Exchange diffusion |
| Glucoheptonate (GH) | Technitium-99 m | Brain, Kidney | Exchange diffusion |
| Pentetate (DTPA) | Technitium-99 m | Lungs | Aerosol |
| Pentetate (DTPA) | Technitium-99 m | Kidney | Simple diffusion |
| Gallium Citrate | Gallium-67 | Tumors, inflammation | Simple diffusion |
| Rose bengal | Iodine-131 | Liver | Active transport |
| Orthoiodohippurate | Iodine-131 | Kidney | Active transport |
| Selenomethionine | Selenium-75 | Pancreas | Active transport |
| thallous chloride | Thallium-201 | Heart muscle | Active transport |

Virtually any pharmaceutical or therapeutic agent may be linked to the organ-specific vectoring reagent by the linking reagent. In particular, therapeutic agents such as antibiotics, anti-cancer drugs, cardiac drugs, analgesics, anti-epileptic agents and vitamins may be utilized. Hormones, white blood cells or monoclonal antibodies may also be linked to the organ-specific vectoring reagent. (White blood cells may even be utilized as the vectoring agent since they are localize at a site of infection or inflammation.)

Furthermore, it should also be noted that the white blood cells or the monoclonals may be included in the composition with another drug such that the conjugate contains four components (or three if the white blood cells are utilized as the vectoring reagent). However, as noted above, the monoclonals or white blood cells may also be administered without the additional drug.

Specific tumor reactive monoclonal antibodies linked with anti-cancer drugs have been used in the past few years in order to deliver the drug to the tumor site (Weinstein et al., *Cancer Metastasis: Experimental and Clinical Strategies*, Alan R. Liss, Inc., 169-80 (1986)). Tumors are generally localized in certain portions of organs and tend to spread to the remaining portions of the organ involved. Thus, conjugates of the monoclonal antibodies and chemotherapeutic drugs, when linked with an organ specific organ-specific vectoring reagent will have a greatly increased chance of vectoring delivery of the drug to the tumor site. For example, lung cancer when detected early involves a part of the lung. Therefore, a monoclonal antibody linked to a chemotherapeutic agent by a lung scanning agent will enhance the efficacy of the drug due to the resulting dual action.

The linking agent may be linked to the medical organ-specific vectoring reagent and the drug by either temporary bonding (i.e., passive absorption bonding) or by permanent bonding (i.e., covalent bonding). In fact, the linking agent may be characterized by the manner in which it bonds to the organ-specific vectoring reagent and drug. The linkage to the organ-specific vectoring reagent and therapeutic agent may be made either temporary or almost permanent by changing either the reaction conditions or the drug/organ-specific vectoring reagent combination utilized. Furthermore, the linking agent of choice depends on the organ to be targeted as well as the drug which is to be delivered to the organ. Cell and animal studies indicate that the thus-conjugated drug entity is released intact, and as an active molecule, from and at the site in the body where the organ-specific vectoring reagent accumulates.

The linking agents to be used in this invention are, of course, biocompatible and have no, or at most, de minimis toxic side effects. Such a suitable linking agent is, for example, L-α lecithin also referred to as phosphatidyl choline or cephaloplastin. The linking agent may also be dissolved in one or more buffers including, for example, phosphate buffered saline, and buffers such as Tris buffer, glycine buffer, Tris-saline buffer (pH 7.4), phosphate buffered saline buffer (pH 7.4), and carbonate/bicarbonate buffer. Furthermore, the linking agent may also be brought to the proper concentration by being mixed with a buffer. The buffer utilized depends on which organ is to be targeted (see, e.g., Example XVII and Table II). As noted above, enzymes such as proteolytic and lipolytic enzymes cause the bonds to break between the linking agent and the organ-specific vectoring reagent. These enzymes also cause the bonds to break between the linking agent and the therapeutic or pharmaceutical agent. Again, the linking agent is attached to the therapeutic or pharmaceutical entity by covalent bonds or by passive adsorption or a combination thereof.

Cephaloplastin was used as the linking agent in the examples shown below, and was dissolved in a suitable buffer. The cephaloplastin was prepared from bovine brain extracted with chloroform and is called Type III-L-α. However, other lecithin or cephaloplastin preparations, and thus linking agents, can be made from, for example, extracts from bovine heart (i.e., Type III-H), from bovine liver (i.e., Type III-L), from dried egg yolk (i.e., Type X-E), from fresh egg yolk (i.e., Type X-I-E), and from soy bean (i.e., Type III-S). These preparations of lecithin may be as effective as the brain derived cephaloplastin utilized in the examples. Other substances may also be suitable linking agents such as, for example, typed blood platelets, Hogeman factor, plasma thromboplastic component, proconvertin, lectins, platelet phospholipids, Thymosin and other brain extracts obtained using chloroform.

Drug delivery based on particle size may be generally more effective when the bond is not covalent but is based on passive adsorption, so that the drug is eliminated at a faster rate. By contrast, if a covalent bond is utilized in forming the conjugate, the drug may reside in the body for a longer period of time. As noted above, whether a covalent bond is formed or whether passive absorption between the linking agent and the drug as well as between the linking agent and organ-specific vectoring reagent can depend on the choice of buffers, temperature and other such variables known in the art.

The conjugate composition containing the organ-specific vectoring reagent, the drug and the linking agent may either be injected into the patient or administered orally. The most effective and thus preferred means of administration is by the intravenous route.

Table II (below) represents a summary of various organs, systems or tissues which can be treated using particular organ-specific vectoring reagents, therapeutic agents, linking agents and combinations thereof. The agents or compounds listed represent examples which are being utilized for illustrative purposes. The present invention is, by no means, limited to the precise compounds listed.

TABLE II

| Group | No | Organ/System/Tissue | Vectoring Agent | Drug/Therapeutic Agent | Linking Reagents |
|---|---|---|---|---|---|
| A | 1 | Brain | 1. Sodium Pentatate (DTPA)<br>2. Glucoheptonate sodium (Stannous glucoheptonate)<br>3. Mercury (Chloro-merodine) | Anticancer drugs, Antiepileptic drugs, CNS Stimulants, Psychotic antidepressants, convulsion medicine, antibiotics, antispasmodic drugs | Cephaloplastin + Phosphate Buffered Saline |
|  | 2 | Liver | 1. Sulfur colloid<br>2. Sodium Phytate<br>3. Gold Colloid<br>4. Stannous HIDA, PIPIDA, DISOFENIN | Anti-Neoplastic drugs, Antibiotics (Tetracycline), Amino acids, Enzymes, Monoclonal abs. | Cephaloplastin & Carbonate/Bicarbonate Buffer |
|  | 3 | Lung | 1. Macroaggregated albumin<br>2. Microspheres<br>3. Xenon gas<br>4. Krypton gas | Anticancer drugs, anticoagulants (Heparin), antibiotics, antiviral drugs (Pentamidine), antituberculosis drugs, vasodilators, broncho-dialators, anticholinergics, asthma preparations, antitoxoplasmosis drugs, monoclonal abs. | Cephaloplastin & Carbonate/Bicarbonate Buffer |
|  | 4 | Kidneys | 1. Mercury (Chlormerodrin)<br>2. Sodium iodobipurate (Hippuran)<br>3. Sodium Pentatate iron ascrobate (DTPA)<br>4. Stannous DTPA<br>5. Stannous glucoheptonate | Antibiotics<br>Diuretics (lasix)<br>Analgesics | Cephaloplastin + Phosphate Buffered Saline |

TABLE II-continued

| Group | No | Organ/ System/Tissue | Vectoring Agent | Drug/ Therapeutic Agent | Linking Reagents |
|---|---|---|---|---|---|
| | | | 6. Stannous dimercaptosuccinic acid | | |
| | 5 | Bone | 1. Polyphosphates<br>2. Sodium Etidronate<br>3. Stannous pyrophosphate<br>4. Sodiummedronate | growth hormone, bone metabolitic agents, antibiotics, pagepic agent, calcium, phosphorus, analgesics, ossification agents, narcotics, anti-arthritic drugs, anti-inflammatory drugs | Cephaloplastin + Phosphate Buffered Saline |
| | 6 | Pancreas | 1. Selenomethionine | MAbs + insulin, enzymes, pancrease, Arcolase, Kuzyme | Cephaloplastin + Phosphate Buffered Saline |
| | 7 | Parathyroid | 1. Selenomethonine | anticancer drugs, hormones, monoclonal abs. | Cephaloplastin + Phosphate Buffered Saline |
| | 8 | Thyroid | 1. Sodium iodide<br>2. Potassium iodide | anticancer drugs, hormones, monoclonal abs. | Cephaloplastin + Carbonate/Bicarbonate Buffer |
| | 9 | Bone Marrow | 1. Sulfur colloid<br>2. Indium chloride | hemopoietic factor, antiviral drugs, anticancer drugs (leukemia), AZT, DDA, Vitamin $B_{12}$, folic acid, antibiotics | Cephaloplastin + Phosphate Buffered Saline |
| | 10 | Spleen | 1. Sulfur colloid<br>2. Indium chloride | anticancer drugs, antibiotics, monoclonal antibodies | Cephaloplastin + Phosphate Buffered Saline |
| | 11 | Heart | 1. Thallium chloride<br>2. Thallous chloride<br>3. Stannous pyrophosphate | alpha adrenoreceptors, agonists, nitroglycerins, antierythmia drugs, indocin, monoclonal abs., vasodilators, coronary and general betablockers, anti-hypertensives, actirose, calcium channel, blockers, anginal preps., streptokinase | Cephaloplastin + Carbonate/Bicarbonate Buffer |
| | 12 | Cerebrospinal fluid compartments | 1. Ytterbium DTPA<br>2. Indium DTPA | antiviral drugs, monoclonal abs. antimicrobials, analgesics, narcotics, opium compounds | Cephaloplastin + Carbonate/Bicarbonate Buffer |
| | 13 | Lymphatic system | 1. Sulfur colloid | antivral drugs, antibacterial drugs, monoclonal abs. | Cephaloplastin + Phosphate Buffered Saline |
| | 14 | Placenta | 1. Human serum albumin | anticancer drugs<br>Antibiotics (Erythromycin) | Cephaloplastin + P.B.S. |
| | 15 | Lung mediastinum | 1. Gallium citrate | antiviral drugs, antimicrobial drugs, anticancer drugs, bronchodialators, vasodilators, antibiotics (Erythromycin) | Cephaloplastin, + Carbonate/Bicarbonate Buffer |
| | 16 | Soft tissue | 1. Gallium citrate | anticancer drugs, antibiotics, anti-inflammatory, antiviral, enzymes, antihyperlipemic drugs | Cephaloplastin + Carbonate/Bicarbonate Buffer |
| | 17 | Eye | 1. Sodium phosphate (soluble) | antiviral drugs, antibiotics | Cephaloplastin + P.B.S. |
| | 18 | Venous vessel clots | 1. Fibrinogen | thrombolytic agents, heparin, activase, streptokinase | Cephaloplastin + P.B.S. |
| | 19 | arterial vessels clots | 1. Fibrinogen | Elase, Granulax, protamin, demser, indocin | Cephaloplastin + P.B.S. |
| B | 20 | Blood | 1. Human serum albumin<br>2. Treated red blood cells | antiviral drug, antiarthritic drug, anticancer drug, vasodilators, antibiotic, hemonetics antihypertensives, anticoagulants, antihyperlipemics, antidotes, antiinflammatories, hormones, antiplatelet drugs (aspirin) | Cephaloplastin + P.B.S. |
| | 21 | Pancreatic function | 1. Neutral fats<br>2. Fatty acids | anticancer, enzymes, insulin | Cephaloplastin + Carbonate/Bicarbonate Buffer |
| | 22 | Gastrointestinal tract | 1. Human serum albumin<br>2. Treated red cells | antiviral, antibiotics, enzymes, digestants, | Cephaloplastin + Carbonate/Bicarbonate |

TABLE II-continued

| Group | No | Organ/System/Tissue | Vectoring Agent | Drug/Therapeutic Agent | Linking Reagents |
|---|---|---|---|---|---|
| | 23 | Anemic Blood | 1. Cyancobalamin cobalt<br>2. Ferrous citrate<br>3. Ferric chloride | hemopoietic, nutrients iron, vitamin $B_{12}$, folic acid, hemonetics, nutrients, proteins | Buffer Cephaloplastin + P.B.S. |

There are several advantages to the novel vectored delivery method of the present invention. In particular, since the therapeutic agent is localized rapidly and directly in the desired organ or tissue of choice, rather than being diluted randomly in the bloodstream, one may administer a reduced dose of the drug. Since many of these drugs, as noted above, have detrimental side effects, by lowering the required dose, one also eliminates many of the side effects and/or the severity thereof. Furthermore, due to the decreased required dosage, one may also administer useful drugs which have hitherto been thought to be too toxic to utilize due to the traditional higher dosages required.

Moreover, in the case of kidney disfunction, for instance, the therapeutic drug may not be excreted as quickly as in the case when the kidneys are functioning properly. Consequently, the disfunction may lead to undesirably high or toxic plasma concentrations with serious side effects. (The same problem also arises with respect to liver disfunction.) Thus, effective drug administration may be complicated. These problems are eliminated or at least substantially reduced upon the use of the present invention as the proper amount of therapeutic agent is delivered to the specific site of interest and dangerous plasma concentrations levels may be avoided.

Also, due to the localization of the drug, one need not administer so called "loading" doses of the drug to the patient. The "loading dose" is the very high initial dose or doses of the drug which are initially administered in order for an effective dose to be reached. Thus, due to the dilution of the drug in the system, many patients are given initially high doses of the drug for several weeks to be followed by maintenance doses. By contrast, if the drug is selectively delivered directly to the tissue or cell of interest, dilution is not a concern and the proper (lower) dosage may be achieved at the outset of treatment. For example, a digoxin level of 0.4 mg/100 ml of blood, an effective dose, may be attained with one administration of the drug using the method of the present invention.

Moreover, since the drug of interest is delivered directly to a particular organ or tissue site, adverse affects of the drug on healthy organs or tissues are avoided. Frequently, when a chemotherapeutic agent is administered to a patient, healthy tissues as well as malignant tissues are destroyed since the drug is widely dispersed in the body tissue through the bloodstream. By way of analogy, if the drug is not targeted and goes into the systemic circulation, it will be dispersed much like acetylsalicylic acid and is routed everywhere in the body, thereby potentially adversely affecting or destroying healthy tissue.

It should also be noted that the present system is particularly advantageous if a patient must be treated with two or more drugs simultaneously, which will typically have different absorption rates. Since the vectored drugs used in the present invention are not diluted by random distribution throughout the system, far accurate drug ratios can be maintained at a particular site, for example, a tumor site.

The present method may be utilized with respect to known imaging and therapeutic agents. Such organ-specific reagents have been routinely used in nuclear medicine departments of hospitals for diagnostic purposes. In particular, such organ-specific reagents are used in performing lung, liver, bone, heart and brain scans. Since the respective imaging and therapeutic agents of the present invention are individually widely available and approved for human use, the vectored conjugate combination composition and method of the present invention can be carried out quite safely and easily, based on the present description of this invention. The present invention is illustrated by use of the following non-limiting examples:

Example I

In Vitro Determination of the Concentration of Cis-Pt in a Conjugate

The cis-Platinum (II) Diammine Dichloride was obtained from Sigma. Conjugation of cis-Platinum was carried out using an aseptic technique (i.e., Cis-Pt was linked to macroaggregated albumin particles greater than 15 $\mu M$ in size using passive adsorption). 20 mg cis-Platinum (II) was dissolved in 5 ml of saline and was further diluted in 15 ml coupling agent (i.e., cephaloplastin dissolved in phosphate buffered saline). 5 mg of the drug in the coupling agent was conjugated with the macroaggregated albumin particles. The resulting mixture yielded >85% conjugated drug and <15% free drug. The recommended dose for cis-Platinum was assessed to be 10 mg/kg. (The dose is determined by mg/kg bodyweight and is established by the manufacturer of each drug.)

Four groups of six male $F_1$ hybrid mice (C57BL/6X DBA/2) 6-8 weeks old (20-25g body weight) were used for the study. Group A received unconjugated cis-Platinum; the second group, B, received cis-Platinum conjugated with the organ-specific vectoring reagent macroaggregated albumin (MAA). Group C received cis-Platinum conjugated with colloidal sulfur particles. Group D was injected with MAA alone, with no cis-Platinum conjugated or unconjugated, and served as controls. Three additional mice were used as normal untreated controls.

Lewis lung murine tumors of the biological type lung carcinoma were implanted subcutaneously in the group B C57BL/6 mice. Colon 38 of the histological type colon carcinoma was implanted in group C57BL/6. Three mice from group A were implanted with Lewis lung tumors and the remaining three were implanted with colon 38 tumors subcutaneously. Three mice from control group D were implanted with Lewis lung tumors and three with colon 38 tumors. This group did not receive any treatment with cis-Platinum in any form.

All experimental animals were injected intravenously (IV) with 0.5 mg doses of cis-Platinum to a final concentration of 2.5 mg/25 g body weight, maximum volume 0.2 mL/mouse. The above protocol was used in Examples II-VI. In Examples VIII and IX, 8 mg/kg doses were administered intravenously.

Cis-Platinum concentration in the conjugate with MAA was compared with cis-Platinum solution used for injection by Zeeman effect flameless atomic absorption spectrophotometer. The value of the cis-Platinum concentration in the cis-Platinum:saline solution was approximately equivalent to 2.5 mg/ml. The value of the cis-Platinum concentration in the conjugate was approximately equivalent to the value of the cis-Platinum concentration in the cis-Platinum:saline solution. In particular, the drug (i.e., Cis-Pt) was effectively (>99%) conjugated to the organ-specific vectoring reagent (MAA). The results are shown below:

|  | Cis-Pt Concentration Cis-Pt MAA conjugate |
|---|---|
| Test Sample 1 | 2.39 |
| Test Sample 2 | 2.50 |
| Test Sample 3 | 2.49 |

EXAMPLE II

EVALUATION OF THE EXISTENCE OF RENAL

Toxicity in Mice Injected with Cis-Platinum and Cis-Platinum-MAA Conjugate

Renal toxicity was assayed by measuring BUN (blood urea nitrogen) after four days of the initial dose. The occurrence of gastrointestinal toxicity was evaluated based on the appearance of diarrhea, a common undesirable side-effect of cis-Platinum treatment. Blood samples were obtained by puncture or retrobital venous plexus (50 uL/sample) before giving the treatment dose.

In particular, on day 1, base level samples were taken from mice in order to determine the concentration of blood urea nitrogen (BUN) in the samples. After taking base line samples, the first dose of 0.5 mg was injected.

On day 2, samples were taken, BUN concentration was checked. The BUN levels were 107 (non-conjugated sample) and 37 (MAA conjugate). The mice were then injected with a second dose of 0.5 mg.

On day 3, samples were again taken (BUN=174 (non-conjugated sample) and 41 (MAA conjugate)), and the mice were injected with 0.5 mg.

On day 4, the BUN concentration was equivalent to 03 (non-conjugated sample) and 30 (MAA conjugate), and a third dose of 0.5 mg was given.

On day 5, the BUN concentration was equal to 122 (non-conjugated sample) and 31 (MAA conjugate), and a fourth dose of 0.5 mg was administered. (On day 6, results were not available or tested as renal toxicity had not been established.)

The results from the five days are shown below:

The above data indicate that greatly reduced renal toxicity was achieved with the conjugate as compared to cis-Platinum alone.

EXAMPLE III

Evaluation of Bone Marrow Toxicity of

Mice Treated with Cis-Platinum Alone and Conjugated with Macroaggregated Albumin After introducing the cis-Platinum and its MAA conjugate (0.5 mg. into each 23-25 g mouse), blood samples were taken on days one to four before and after treatment and on days 5, 10, and 21 after the last dose. The total number of nucleated cells, that is, the total number of total white blood cells, was counted with a Coulter counter and a blood film was prepared simultaneously for lymphocyte-to-neutrophil (L/N) ratio.

More specifically, the mice received four doses (i.e., one each day for four days). Baseline white blood cell (WBC) counts were done on day 0. It takes 4-5 days for bone marrow toxicity to occur if it is actually going to occur; thus, on day 5, counts were taken (see below, 9.8 vs. 10.1). Counts were also taken on day 10 and day 21.

The results obtained from the experiment are shown below:

| | BONE MARROW TOXICITY | | | |
|---|---|---|---|---|
| | AFTER 4 DAILY DOSES (0.5 mg. ea) cis-Pt | | AFTER 4 DAILY DOSES. (0.5 mg. ea) cis-Pt MAA | |
| DAY | WBC $10^3$ cells/dL | L/N | WBC $10^3$ cells/dL | L/N |
| 0 | 9.8 +/− 0.6 | 8.0 +/− 1.8 | 10.1 +/− 0.6 | 8.1 +/− 0.2 |
| 5 | 5.1 +/− 0.3 | 3.3 +/− 0.5 | 9.1 +/− 0.5 | 7.9 +/− 0.2 |
| 10 | 2.6 +/− 0.2 | 1.6 +/− 0.2 | 8.7 +/− 0.3 | 7.3 +/− 0.3 |
| 21 | 1.4 +/− 0.2 | 1.0 +/− 0.1 | 8.5 +/− 0.2 | 7.1 +/− 0.3 |

The results above indicate that greatly reduced bone marrow toxicity was achieved with the conjugate as compared to cis-Platinum alone.

EXAMPLE IV

Comparison of Liver Function Tests on Blood Samples Treated With Cis-Platinum Solution and Cis-Platinum Macroaqqreqated Albumin Solution Liver function tests were performed on blood samples after ten days of treatment with the solutions (see Example III). Four doses were administered each day.

| | Liver Function Tests | |
|---|---|---|
| Test | cis-Pt | cis-Pt-MAA |
| SGOT | 120 | 20 |
| SGPT | 112 | 12 |
| Serum bilirubin | 3.8 | 1.0 |
| Serum albumin | 3.8 | 3.8 |
| Prothrombin | 16 | 16 |

| | | | RENAL TOXICITY | | | | |
|---|---|---|---|---|---|---|---|
| DAY NO. | NO. DOSES | cis-Pt DOSE mg | BUN mg/dL | DIARRHEA | cis-Pt-MAA DOSE mg | BUN mg/dL | DIARRHEA |
| 1 | 0 | 0.0 | 26 +/− 5 | NO | 0.0 | 22 +/− 4 | NO |
| 2 | 1 | 0.5 | 107 +/− 24 | NO | 0.5 | 37 +/− 7 | NO |
| 3 | 1 | 0.5 | 174 +/− 35 | NO | 0.5 | 41 +/− 7 | NO |
| 4 | 4 (1/day) | 0.5 | 103 +/− 13 | NO | 0.5 | 30 +/− 3 | NO |
| 5 | 5 (1/day) | 0.5 | 122 +/− 21 | NO | 0.5 | 31 +/− 8 | NO |

| Liver Function Tests | | |
|---|---|---|
| Test | cis-Pt | cis-Pt-MAA |
| clotting time | | |

(SGOT = serum glutamic organic transaminase. SGPT = serum glutamic pyruvate transaminase)

The data indicates that the conjugate exhibited minimal impairment of the function of the liver.

EXAMPLE V

Antitumor Effect of Cis-Platinum and Cis-Platinum-MAA Conjulate

The antitumor activity of both solutions was tested in vitro. Colon 38 tumors were used for in vitro screening of the antitumor effect. Tumors were place in 10ml solution of each of the agents. The tumors were removed after 21 days of culture growth and examined for weight loss and shrinkage in size. The results are shown below:

| ANTITUMOR TESTS, IN VITRO | | |
|---|---|---|
| Test | cis-Pt | cis-Pt-MAA |
| Shrinkage | 41% | 37% |
| Weight loss | 63% | 59% |

Comparable results were obtained with the use of cis-Pt alone and with the use of the conjugate. Thus, an equally effective dose response results from the use of both compounds.

EXAMPLE VI

Biodistribution of Cis-Platinum and Cis-Platinum-MAA Conjugate

Thirty minutes after injecting the mice with either agent, one millicurie of technicium Tc-99 m was injected IV and the mice placed under a gamma camera to trace the cis-Platinum. The mice treated with cis-Platinum exhibited an even distribution of the radioisotope in all organs in the abdomen. Those treated with cis-Platinum-MAA conjugate showed an almost 90% in vivo labeling of MAA in the lung. Most of the remaining activity was seen in the kidney and bladder with some in the heart (<3%).

Similar patterns of activity were seen when both groups of mice were injected after three days. Cis-Platinum-MAA conjugated material continued to be visualized in the lung after three days indicating the presence of maximum concentration of the conjugated drug in the lung.

EXAMPLE VII

Conjugation of Cis-Platinum (II) Diammine Dichloride with Microlite

The cis-Platinum (II) Diammine Dichloride was obtained from Sigma, and Microlite was obtained from DuPont. (Microlite is a tradename for a liver organ-specific reagent. It contains albumin particles less than 5 µM in size.)

Conjugation of cis-Platinum was carried out using an aseptic technique (i.e., Cis-Pt was linked to albumin particles as contained in Microlite using passive adsorption). 20 mg cis-Platinum (II) was dissolved in 5 ml of saline and was further diluted in 5 ml coupling agent. 5 mg of the drug in the coupling agent was conjugated with Microlite. The resulting mixture yielded 57% conjugated drug and 43% free drug. Recommended dose for cis-Platinum was assessed to be 10 mg/kg. (The dose is determined by mg/kg bodyweight and is established by the manufacturer of each drug.) This preparation was used in the following examples VIII and IX.

The following examples VIII and IX illustrate generally comparable antitumor efficacy for conjugated cis-Platinum (according to this invention) as compared with cis-Platinum used as such. These examples show that binding the cis-platinum in the conjugate does not materially, if at all, inhibit the efficacy of the therapeutic agent.

EXAMPLE VIII

Effect of Cis-Platinum versus Cis-Platinum-Conjugate on In Vivo Tumor Cells $10^4$ L1210 leukemia cells were transplanted intravenously (iv) into DBA mice. Three days later the animals received 8 mg/kg cis-Platinum in saline or 8 mg/kg cisplatinum-conjugate administered (iv) (3 animals/group)

| | Death Day | Incr. Life Span (ILS) |
|---|---|---|
| Control | 11, 12, 13 | |
| 8 mg/kg cis-Pt saline | 20, 28, 28 | 111% |
| 8 mg/kg cis-Pt conjugate | 17, 22, 23 | 72% |

Basically, the two solutions yielded similar results. Individual subjects or unknown factors may have caused the two 28 death day mice to live longer than the conjugate mice.

The toxicity experiment was performed on non-tumored DBA mice with the drugs administered i.v. (3 animals/group).

| | Cisplatinum Saline Death Day | Cisplatinum Conjugate Death Day |
|---|---|---|
| 20 mg/kg | 8, 8, 10 | 5, 7, 8 |
| 15 mg/kg | 7, 10, >30 | 7, >30, >30 |
| 12.5 mg/kg | 10, 10, >30 | 8, >30, >30 |
| 10 mg/kg | >30, >30, >30 | >30, >30, >30 |

The above example demonstrates the anti-tumor effect of conjugated cis-Platinum as compared to cis-Platinum alone. 10 mg/kg dose was considered optimal. The 12.5 mg, 15 mg and 20 mg doses were actually excess doses which may have caused earlier death in some mice due to side effects or other complications which are not yet explained.

EXAMPLE IX

Effect of Cisplatinum Versus Cisplatinum Conjugate on Mice Implanted with Leukemia Cells DBF mice were planted intraperitoneally with $10^4$ K1210 leukemia cells. Three days later, 8 mg/kg of cis-Platinum in saline and cis-Platinum conjugate preparation was given intravenously via a tail vein.

| | Death day | % ILS |
|---|---|---|
| Control | 10, 10, 10 | |
| cisplatinum saline treated | 14, 20, 20 | 80% |
| cisplatinum conjugate treated | 16, 16, 17 | 63% |

Both preparations clearly had anti-tumor activity (minimum of 20% increased life span is considered active). The results are relatively comparable. Again, individual subjects or unknown factors may have contributed to the increased ILS percentage with respect to the cis-Platinum group. (57% of the cis-Platinum was conjugated with albumin particles.)

Reduced toxicity, while retaining therapeutic effectiveness, was clearly the advantage with the conjugate as compared with cis-Platinum saline administrations.

In this Example, only 57% of the total dose was available in the conjugate. The conjugate results were considered to be equivalent to the saline solution results. Even with a 43% reduction in dose, equal therapeutic effectiveness was achieved as with the saline solution.

It is evident that if the conjugation was improved better than 57%, the anti-tumor effect may still be more significant as more of the anti-tumor agent would reach the tumor. Improved linking provides a better drug to carrier (i.e., organ-specific vectoring reagent) ratio. Moreover, a further decrease in toxicity and increase in ILS may also be achieved.

EXAMPLE X

Composition A

Drugs/Antibodies Targeted to an Organ or Tissue Which Retain Exogenous Substances By Capillary Blockage Mechanism of Uptake Based On Particle Size (i.e., the Lung)

Albumin particles with a size range of between 15-30 $\mu M$ or larger will pass through the heart and thus into the capillary bed of the lungs where they will deposit with 99% efficiency.

Albumin particles with a smaller size range of 114 3 $\mu M$ when injected intravenously will pass into the reticuloendothelial system where they will deposit with about 90% efficiency in the liver.

Albumin particles with a size of less than 1 $\mu M$ in diameter result in a mixed distribution of the tiny particles among the liver (80-90%), spleen (5-8%) and bone marrow (1-2%).

The targeting of albumin particles to these respective organs or tissues can therefore be accomplished on the basis of size alone and by simple intravenous injections. Drug-linked albumin particles targeted to other organs can be deposited by using specialized angiographic methods. Similar vectored delivery can be achieved with respect to the specific sites within an organ or to a solid tumor.

The rate of drug release from injected albumin particles and the rate at which albumin particles degrade in the body are controlled by the degree of cross-linking. Cross-linking can be accomplished by heat denaturation of albumin or by chemical methods including adding formaldehyde and glutaraldehyde to the linking agent 1 described in Example XIV.

Shown below is a composition containing aggregated albumin as the organ-specific vectoring reagent.

| Composition A Unit Dose: Sterile, Pyrogen free | | |
|---|---|---|
| Ingredient | Optimal Conc. | Range |
| Aggreg. Albumin (0.5-1.0 × 10⁶ particles) | 0.11 mg | 0.2-100 mg |
| Stannous Tartrate (or stannous chloride stannous fluoride) | 0.09 mg | 0.001-1.0 mg |
| Total tin Content | 0.17 mg | 0.01-1.0 mg |
| Isotonic saline (PBS) pH 7.4 | 0.3 ml | 0.01-5 ml |
| Plus a Linking Mixture (see Ex. XIV) | | |
| Plus an Antibody | | |
| Plus a drug (i.e., cis-Platinum or an antibiotic) | | |

Composition A yielded cis-Platinum conjugated MAA particles with a size ranging from 15-30 $\mu M$ with 99% drug to carrier binding efficiency and greater than 85% deposition in lung capillaries.

EXAMPLE XI

Composition B

Applicable to Organs which Retain Drug by Phagocytosis Mechanism of Uptake (for Example, Liver, Spleen & Bone Marrow)

| Ingredient | Optimal Conc. | Range |
|---|---|---|
| 1. Colloidal sulphur or coll. albumin | 1 mg | 0.1-5 mg |
| 2. Normal Human Serum Albumin | 10 mg | 0.1-100 mg |
| 3. Stannous Chloride | .006 mg | 0.001-6 mg |
| 4. Total Tin | 0.17 mg | 0.004-4 mg |
| 5. Poloxamer 188 | 1.1 mg | 0.005-5 mg |
| 6. Medronate Disodium (anhydrous) | 0.17 mg | 0.01-5 mg |
| 7. Sodium Phosphate | 10.0 mg | 0.1-50 mg |

Composition B yielded cis-Pt conjugated sulphur colloidal particles with size range of 1-8 $\mu M$ with 99% drug to carrier binding efficiency and greater than 85% deposition in Kupfer cells of liver, 6% in the spleen and about 1% in the bone marrow.

EXAMPLE XII

Composition C

A composition Comprising a Vectoring Agent, Linking Agent and Drug/Antibody Used to Target An Organ Which Retains Drug by Adsorption (i.e., Bones)

| 2 variations of the same composition | | |
|---|---|---|
| a. Unit Dose | | |
| 1. Medronate DiSodium | 2.0 mg | 0.2-10 mg |
| 2. Stannous Chloride | 0.005 mg | 0.005-.015 mg |
| 3. Total Tin | .0010 mg | 0.001-1.0 mg |
| 4. Linking Agent & Drug/Antibody | | |
| b. | | |
| 1. Medronic Acid | 4.0 mg | .04-10 mg |
| 2. Sodium Hydroxide | 2.0 mg | 0.2-10 mg |
| 3. Ascorbic Acid | 0.02 mg | 0.02-5 mg |
| 4. Stannous Chloride | 0.06 mg | .06-1.0 mg |
| 5. Linking Agent & Drug/Antibody | | |

EXAMPLE XII

Composition D

Applicable to Organs Which Retain Drug by Simple Diffusion (i.e., kidney)

| Pentatate PentaSodium | 1 mg | 0.1–5 mg |
|---|---|---|
| Stannous Chloride (Stannic Chloride) | 0.275 mg | 0.006–0.5 mg |
| Linking Agent & Drug W/ or W/0 Antibody -applicable to tumors, inflammation and infections | | |
| Gallium Citrate = imaging agent applicable to soft tissue (i.e., tumors, inflammation, infections) | | |

EXAMPLE XIV

Composition E

Reaction Mixtures Containing Linking Agent

| 1. | P.B.S. | pH 7.4 |
|---|---|---|
| | Gelatin | 0.1 mg/ml |
| | Sucrose | 0.05% |
| | Cephaloplastin with Lecithin (phospholipid) | 0.05 mg/ml |
| 2. | Carbonate/Bicarbonate | |
| | Buffer | pH 9.0 |
| | Gelatin | 0.1 mg/ml |
| | Sucrose | 0.05% |
| | Cephaloplastin & Lecithin (phospholipid) | 0.05 mg/ml |
| 3. | Tris - saline buffer 0.6 gm Tris/100 ml, | pH 7.4 |
| | Gelatin | 0.1 mg/ml |
| | Sucrose | 0.05% |
| | Cephaloplastin & Lecithin (phospholipid) | 0.05 mg/ml |

The choice of one of the above reagents is based upon the organ to be targeted and the drug to be administered.

EXAMPLE XV

Use of Linking Agent of Example XIV to Bind Vectoring Reagent to Drug of Choice For the Targeting of Organs Which Retain Drug by Active Transport

| | Vectoring Reagent |
|---|---|
| Heart Muscles | Thallous Chloride |
| Pancreas | Selenium Seleniomethionine |
| Kidney | Methodiobippurate |
| Liver | Rose Bengal |
| Liver/Gall Bladder | Disofenin DISIDA |
| + Stannous Chloride + Linking Agent | |

Composition E will bind imaging agents for different organs based on active transport mechanisms.

EXAMPLE XVI

Use of White Blood Cells as Vectoring Reagent

White blood cells can be substituted for albumin aggregates. (Use composition A, Linking Agent & Drug-/Antibody. See Ex. X.)

In particular, cis-Pt, for example, can be conjugated with an antibiotic and leukocytes. The efficiency of tagging can be 85–96%. The mechanism of action is based on the direct migration of polymorphonuclear leukocytes to the site of infection or tumor (i.e., abdomen, liver, uterus, ovaries, ulcers, lymphosarcoma of intestines, etc.)

This therapeutic approach can also be utilized in the treatment of a fever of an unknown origin, intra-abdominal abscesses, renal inflammatory disease, inflammatory bowel disease, acute osteomyelitis, soft tissue infection, intervertebral disk infection, graft infections, acute inflammations, and for the evaluation and treatment of sarcoidosis.

EXAMPLE XVII

Conjugation of Anti-Tumor Drug Bleomycin With Lung Targeting Agent, Macro agggregated Albumin (Particle Size 15–30 microns)

Reagents Used:
1) Lung Targeting Agent containing MAA, $SnCl_2.2H_2O$.
2) Linking Agent
3) Bleomyin (Bleomycin (BLM) complexes with various radioactive metals such as $Ga^{67}$, $Co^{57}$, $In^{111}$, $Hg^{197}$, $Pl^{203}$, $Cu^{64}$, $Fe^{59}$, and $Tc^{99}$ have been used as scintigraphic agents for visualization of tumors (Nouel et al., Monogr. Cancer Res. 19:301 (1976).

Bleomycin was obtained as sterile lyophilized powder. Its chemical form is a chloro or ½ sulfate of BLM-$A_2$ and BLM-$B_2$ (2:1) ratio. Analytical systems employed included thin layer chromatography (TLC) and electrophoresis (EP). TLC was performed with Merck Silica gel with 10% (w/v) $NH_4OAc$: MeOH (1:1) as solvent. EP was carried out with TOYON030 filter paper as electrophoretic apparatus at constant voltage (500 V) with 0.2 M phosphate buffer (pH 7.0). 7.5 mg BLM was dissolved in 1 ml of linking solution (see Example X, Composition A). 0.1 ml Snelz solution ($SnCl_2$ solution (stannous chloride solution)) (2–2.5 mg., $1 \times 10^{-11}$ M) in 0.1 M PBS, pH 5.6)) was added to BLM and the linking solution and the mixture was subjected to nitrogen bubbling for 10 minutes. Ascorbic acid ($1 \times 10^{-4}$) was added and the mixture was stirred for 10 minutes. The BLM reagent thus prepared was added to one unit dozen vials of lung agent as obtained commercially from NEN-Dupont. The mixture was incubated at room temperature for 30 minutes with regular mixing by gentle inversion. The BLM lung agent (MAA) conjugate was analyzed for conjugating efficiency and free BLM by TLC and EP after 1 and 6 hours. The organ distribution was studied in EHRLICH tumor bearing mice (ddy), weighing 25–30 gm. They were injected with 0.2 ml of the conjugate BLM-MAA. Tumors were transplanted on the left flank and weighed approximately 1 g at the time of the experiment.

High conjugation efficacy was achieved as analyzed on TLC, Rf value of >0.9, at BLM amount of 7.5 mg./ml linking agent. EP results indicated that there was no change in drug activity and conjugation efficiency between (0.5–0.7 cm migration) one to six hours indicating that a chemically stable preparation was obtained. In vivo distribution of BLM-MAA conjugate was studied by in vivo labelling of the conjugate with $Tc^{99}O_4$. The lungs retained the highest dose of the conjugate whereas tumors were the next highest recipient of the conjugate. The highest accumulation of the conjugate in the tumor was detected after 24 hours whereas the lungs retained the conjugate for less than eight hours in this preparation. Low activity in the stomach was considered negligible when compared with the results of drug concentration in lungs and tumor. Conclusion: Antitumor drug Bleomycin was effectively conjugated and delivered to the target organs (lungs) and tissue (tumor). The high degree of conjugation and chemically stable conjugate of Bleomycin with MAA was obtained, indicating possible use of MAA as a carrier for anti-tumor drugs and/or monoclonal antibodies and drug conjugates.

EXAMPLE XVIII

Conjugation of Heparin With Lung Targeting Agent (MAA)

The method of Example XVII was used to conjugate 1000 units of Heparin with MAA (unit dose in final solution =1 ml) 0.1 ml of the unit dose was injected in Balb/C mice. Mice were sacrificed and sections of the lung tissue were examined for the presence of Heparin using Heparin antibody labelled with fluorescein. Results: The presence of Heparin in the lung tissue sections indicated delivery of heparin to the lung capillaries.

EXAMPLE XIX

Conjugation of Ampicillin With MAA 250 mg of Ampicillin was conjugated with (MAA) lung agent and the method of Example XVII was followed. The presence of Ampicillin in the lung tissue sections indicated delivery of the antibiotic to the lung capillaries and tissue. 0.3 ml of the conjugate was added to 2 nutrient agar plates. Streptococcus was inoculated on the plates and the plates were incubated for 24 hrs. at 37° C. Absence of growth in either plate indicated that the drug was still active compared to the lung agent; thus, the drug was still actively conjugated to the lung agent.

EXAMPLE XX

Heat Cross-Linking Method

Macroaggregated Albumin particles were dissolved in linking solution 1 of Example XIV to achieve a final protein concentration of about 25 w/v. 5.0 ml of this solution were injected with a 25 gauge hypodermic needle into 1 liter of stirred cotton seed oil which was preheated to 30°-50 ° C. The mixture was stirred at 500 rpm with a 2.5 inch propeller type stirrer. A water-in-oil emulsion was formed which contained particles having a size of 10-20 $\mu$m. Slower stirring yielded larger particles, and faster stirring yielded smaller particles. Stirring was continued while the temperature of the oil bath was raised to 16 ° C. or higher until the particles were dehydrated. The particles were then filtered on filter paper and washed with di-ethyl ether.

The particles obtained were 10-20 $\mu$m in size and were unagglomerated, free flowing and in powder form. They were insoluble in water but swelled in water. Swelling was inversely proportional to the extent of the heat cross-linking.

EXAMPLE XXI

Relationship Between Biodegradability of Heat Cross-Linked Particles and Temperature of Stabilization

| Temp. | Cross Linking Time | Stability |
|---|---|---|
| 75° C. | 1 hr. | 2 hrs |
| 135° C. | 1 hr. | 24 hrs. |

| Temp. | Cross Linking Time | Stability |
|---|---|---|
| 160° C. | 1 hr. | 84 hrs. |
| 170° C. | 1 hr. | 4 days |
| 190° C. | 1 hr. | 30 days |
| 180° C. | 18 hrs. | 6 months |

Based on the heat cross-linking temperature and the time, it is possible to tailor the time-degradation characteristics of the particles. The size of the particles can be controlled by altering the speed of the stirring.

EXAMPLE XXII

Method of Conjugating Anti-Tumor Drug Cis-Platinum With Macroaggregated Albumin Particles One gram of human-serum albumin was dissolved in 2.0 ml of composition A and water with a magnetic stirrer. 0.1 grams of cis-Platinum was added and stirring was continued for 15 minutes. The mixture was homogenized to obtain a homogeneous distribution of the undissolved drug (i.e., cis-Platinum).

The mixture was injected or added with a tuberculin syringe using a 20 gauge needle to 500 ml of cotton seed oil and stirred at 2500 rpm using a 1.5 inch propeller type stirrer. The temperature was raised to 180° C., and the stirring was continued for 18 hrs.

The oil bath contents were cooled to room temperature and the resulting drug conjugated particles were filtered on Whatman No. 5 filter paper using vacuum filtration. The drug-conjugated particles are then washed several times with 20 ml aliquots of heptane.

The particles contained about 9.6% (w/w) cis-Platinum and albumin in unagglomerated free-flowing powder form with a particle size ranging from 10-50 $\mu$m.

The anti-cancer drug 5-Fluorouracil can also be utilized in the above example in place of Cis-platinum.

EXAMPLE XXIII

Method of Conjugating Ampicillin With Macroaggregated Albumin Particles

The method of Example XXIII was repeated using 250 mg of Ampicillin. Over 80 mg (w/w) of Ampicillin was obtained which was conjugated with the Macroaggregated Albumin particles (MAA).

EXAMPLE XXIV

Method of Conjugating L-Epinephrine With MAA Particles

The method of Example XXIII was repeated using 0.1 gm of L-Epinephrine. About 30 mg of the drug was conjugated to the MAA particles. Thereby a linkage may be established between L-Epinephrine and MAA.

EXAMPLE XXV

Cechaloplastin Linking Agent

The present invention may utilize, for example, cephaloplastin also know as cephalin, liquid brain cephaloplastin or platelet factor. In this invention, this compound is an essential agent for coupling medical organ-specific vectoring reagents such as those described in Table I with therapeutic agents and monoclonal antibodies or a combination of both as described in Table II.

Preparation of Cephaloplastin:

Cephaloplastin is extracted from mammalian brain tissue by the procedure described by Bill et al. in *Nature* 174:880-81 (1954). Rabbit brain is ground up in mortar with about 50 ml of acetone. The acetone solution is decanted, and the same process if grinding and washing with acetone is repeated until acetone washing is free from cholesterol as indicated by a negative Leibermann-Burchardt reaction. The acetone is dried and tissue is extracted with 50-100 ml of chloroform. Two-three extractions yield a residue of 300-400 mg. of cephaloplastin. The residue is then homogenized in about 25 ml of aqueous isotonic NaCl to give derived extract called cephaloplastin or platelet factor. (Cephaloplastin is available commercially.)

In preparing the linking agent for use in the present invention, cephaloplastin (as described above) is diluted in a suitable buffer as described in Example XIV. The therapeutic agent and/or monoclonal antibody is added to the linking agent in order to obtain a conjugate.

It should be noted that carbohydrates like sucrose and gelatin enhance the linking properties of cephaloplastin. Methyl cellulose, ethyl alcohol, aluminum monostearate, glucose and electrolytes may also be added in certain non-particles size based preparations.

EXAMPLE XXVI

Linking of the Hormone Progesterone With Organ-specific vectoring reagents for Delivery to Target Organs (e.g., Bones)

Thirty-nine mg of finely divided progesterone were added to 2.4 ml of linking agent containing Composition C and injected into mice (see Example XII). The drug was examined for its presence in bones after 2days by taking sections of bone from ribs and staining the sections with monoclonal antibodies to progesterone using the Alkaline Phosphatase and Alkaline Phosphatase (APAAP) labeling system as described by Cordell et al. in *J. Histochem. Cytochem.* 32:219 (1984). The results indicated that progesterone was effectively delivered to the bones and was retained up to 21 days as an active molecule.

EXAMPLE XXVII

Linking of Recombinant Growth Hormone With A Organ-specific Vectoring Agent for Delivery to Target Organ The method of Example XXVI was repeated using recombinant growth hormone (rGH). The presence of growth hormone in the bones was detected by using a portion of the femur, taking sections thereof, and staining with monoclonal antibody to rGH using the APAAP (Alkaline Phosphatase and Anti-Alkaline Phosphatase) method described above. The results indicated that the rGH was effectively delivered to the bones and retained for up to 21 days.

EXAMPLE XXVIII

Method of Estimating Drug Release In Vitro by Column Elution Method

Using the conjugate prepared in Example XXVI, the drug release was estimated in vitro by the column elution method described below.

2.0 ml of deionized water was added to 11.6 mg of dry (lyophilized) conjugate as prepared in Example XXVI. The slurry was pipetted into 140 ×7 mm glass columns. The ends of each of the columns were filled with chromatographic caps packed with glass wool. The ends were then attached to threaded zero-volume collectors and connected to 10 mm 1:0 teflon tubing. The columns were placed in a circulating water bath at 37 ° C. Saline was pumped through columns at 0.4 ml/min flow rate with an HPLC pump (ALTEX 110A). Fractions were collected as a function of time at 4° C. and analyzed by uv/vis spectroscopy method. Results: Approximately 20% drug release was found in samples taken after 14 hrs.

EXAMPLE XXIX

Coupling of Monoclonal Antibodies to MAA Particles

Using the procedure of Example X, 1 mg. of monoclonal antibody against HLA-BWG was added to Composition A. The mixture was incubated at 37° C. for 1 hr, and the conjugates thus prepared were injected into mice. Lung tissue sections were stained using the Avidin-biotin HLA-BWG conjugate method (see Guezdom et al., *J. Histochem. Cytochem.* 27:1131 (1979) & Kandizio et al., J. Cancer Res. Clin. Oncol. 101:165 (1981)). The results obtained establish that monoclonal antibodies can be effectively linked with the lung organ-specific vectoring reagent (MAA) and selectively delivered to the lung capillary bed.

EXAMPLE XXX

Coupling of Monoclonal Antibodies to Lung Target-Specific Vectoring Reagent MAA Previously Conjugated to Cis-Platinum Using the method of Example I, cis-Platinum MAA conjugate was used to link the monoclonal antibody as described in Example XXIX. The results were analyzed similarly for the presence of HLA BWG, leading to comparable selective delivery.

EXAMPLE XXXI

Delivery of Pentamidine to Lungs

The method of Example X was used to deliver Pentamidine (5 mg/kg dose) to rat lungs in which *Pneumocystis carnii* pneumonia had been induced by corticosteroid immunosuppression. The high dose effect of the drug was demonstrated in both prophylactic and therapeutic treatment. High lung/kidney and lung/liver ratios of Pentamidine were demonstrated by good chemical, biological, and histological tolerance.

What is claimed is:

1. A composition for the vectored selective delivery of a therapeutically-active agent to a desired mammalian target system, organ, tissue or cell comprising a conjugate composed of a pharmaceutically-acceptable non-toxic organ-specific, non-antibody vectoring reagent selective for said organ tissue or cell, a linking agent entity, comprising cephaloplastic, coupled thereto and a therapeutically active-agent coupled to said linking agent, said conjugate being capable of releasing said therapeutically active-agent with retention of its therapeutic activity to said organ, tissue or cell and wherein said vectoring reagent and said linking agent are coupled by passive adsorption, covalent bonding or a combination thereof, and said linking agent and said therapeutically active agent are also coupled by passive adsorption, covalent bonding or a combination thereof.

2. The composition of claim 1 wherein said non-antibody vectoring reagent is selected from the group consisting of: aggregated albumin, albumin colloid, disofenin, eitdronate, phosphate, sulfur colloid, succimer glucoheptonate, pentetate, gallium citrate, rose bengal, white blood cells, orthoiodohippurate, selenomethionine and thallous chloride.

3. The composition of claim 1 wherein said therapeutically active-agent is selected from the group consisting of: antibiotics, anti-cancer drugs, cardiac drugs, analgesics, anti-epileptic drugs, vitamins, and hormones.

4. The composition of claim 1 wherein said non-antibody vectoring reagent is aggregated albumin, said therapeutic agent is an anti-cancer drug, and said organ is the lung.

5. The composition of claim 1 wherein said composition is administered either orally or intravenously.

6. A method of delivering a therapeutically active-agent to a target organ, tissue or cell of a patient for therapeutic activity in said organ, tissue or cell comprising administering, to said patient, a composition comprising a conjugate composed of a pharmaceutically-acceptable non-toxic organ-specific, non-antibody vectoring reagent selective for said organ, tissue or cell, a linking agent entity, comprising cephaloplastic, coupled thereto and said therapeutically-active agent coupled to said linking agent, said conjugate being capable of releasing said therapeutically active-agent with retention of its therapeutic activity to said organ, tissue or cell, said composition being administered in an amount sufficient to effect said delivery and said therapeutic effect, wherein said vectoring reagent and said linking agent are coupled by passive adsorption, covalent bonding or a combination thereof, and said linking agent and said therapeutically active agent are also coupled by passive adsorption, covalent bonding or a combination thereof.

7. The method of claim 6 wherein said organ, tissue or cell is selected from the group consisting of: brain, liver, lung, kidney, bone, pancreas, parathyroid, thyroid, bone marrow, spleen, heart, cerebrospinal fluid compartments, lymphatic system, placenta, lung mediastinum, soft tissue, eye, venous vessel clots, arterial vessel clots, blood, and gastrointestinal tract.

8. The method of claim 6 wherein said non-antibody vectoring agent is selected from the group consisting of: aggregated albumin, albumin colloid, disofenin, etidronate, phosphate, sulfur colloid, succimer, glucoheptonate, pentetate, gallium citrate, rose bengal, orthoidohippurate, selenomethionine and thallous chloride.

9. The method of claim 6 wherein said therapeutically active-agent is selected from the group consisting of: antibiotics, anti-caner drugs, cardiac drugs, analgesics, anti-epileptic drugs, vitamins, and hormones.

10. The method of claim 6 wherein said non-antibody vectoring agent is aggregated albumin, said therapeutically active-agent is an anti-cancer drug, and said organ is the lung.

11. The method of claim 6 wherein said composition is administered wither orally or intravenously.

12. A method of treating cancer in a patient comprising administering to said patient an amount of a composition for the vectored selective delivery of a chemotherapeutically-active agent to a mammalian target system, organ, tissue or cell, said composition comprising a conjugate composed of a pharmaceutically-acceptable non-toxic organspecific, non-antibody vectoring reagent selective for said organ, tissue or cell a linking agent entity, comprising cephaloplastic, coupled thereto and a chemotherapeutically-active agent coupled to said linking agent, said conjugate being capable of releasing said chemotherapeutically-active agent with retention of its therapeutic activity to said organ, tissue or cell, said composition being administered in an amount sufficient to effect said treatment wherein said vectoring reagent and said linking agent are coupled by passive adsorption, covalent bonding or a combination thereof, and said linking agent and said therapeutically active agent are also coupled by passive adsorption, covalent bonding or a combination thereof.

* * * * *